United States Patent
Tsuboi

(10) Patent No.: US 9,581,555 B2
(45) Date of Patent: Feb. 28, 2017

(54) EGG CANDLING DEVICE

(71) Applicant: AIPI SERVICE LLC, Tokyo (JP)

(72) Inventor: Joichiro Tsuboi, Kumamoto (JP)

(73) Assignee: AIPI SERVICE LLC., Tokyo (JP)

( * ) Notice: Subject to any disclaimer, the term of this patent is extended or adjusted under 35 U.S.C. 154(b) by 9 days.

(21) Appl. No.: 14/435,871

(22) PCT Filed: Oct. 22, 2012

(86) PCT No.: PCT/JP2012/006738
§ 371 (c)(1),
(2) Date: Apr. 15, 2015

(87) PCT Pub. No.: WO2014/064727
PCT Pub. Date: May 1, 2014

(65) Prior Publication Data
US 2015/0293033 A1    Oct. 15, 2015

(51) Int. Cl.
*G01N 33/08* (2006.01)
*G01N 21/95* (2006.01)
(Continued)

(52) U.S. Cl.
CPC ............ *G01N 21/951* (2013.01); *F21S 8/028* (2013.01); *G01N 21/85* (2013.01);
(Continued)

(58) Field of Classification Search
CPC .............................. G01N 33/08; G01N 33/085
See application file for complete search history.

(56) References Cited

U.S. PATENT DOCUMENTS

| | | | | |
|---|---|---|---|---|
| 1,500,939 A | * | 7/1924 | Howell | ................... B65B 23/08 294/87.12 |
| 2,714,523 A | * | 8/1955 | Bliss | ....................... B65B 23/08 119/329 |

(Continued)

OTHER PUBLICATIONS

Internet Translation of JP 2008-256424 A.*

*Primary Examiner* — Kara E Geisel
*Assistant Examiner* — Shawn Decenzo
(74) *Attorney, Agent, or Firm* — Wenderoth, Lind & Ponack, L.L.P.

(57) ABSTRACT

An egg candling device according to the present invention includes at least an egg input and alignment unit for installing trays with eggs to be tested taken out from an incubator on a transporting means. An egg candling unit determines goodness or badness of eggs to be tested in the tray transported from the egg input and alignment unit, and specifies defective eggs. A disposal unit picks up the eggs determined as defective eggs in the egg candling unit. The egg candling unit includes light sources arranged above, a lift unit for lifting up the eggs to be tested installed below the tray and causing the eggs under test to contact the light source. A determining unit determines the goodness or badness of the eggs illuminated by the light source. A notification means specifies the position of the egg determined as a defective egg by the determining unit, and notifies the position to a disposal unit. The lift unit includes an egg holding base having a smaller diameter than diameters of eggs to be tested, a moving means for moving the egg holding base up and down, a tested egg holding unit has plate-like elastic members provided around the egg holding base at specific intervals and extending at a specific length above from the egg holding base.

6 Claims, 6 Drawing Sheets

(51) Int. Cl.
*G01N 21/85* (2006.01)
*G01N 21/88* (2006.01)
*F21S 8/02* (2006.01)
*F21V 8/00* (2006.01)
*F21W 131/411* (2006.01)

(52) U.S. Cl.
CPC ......... *G01N 21/8806* (2013.01); *G01N 33/08* (2013.01); *G02B 6/0006* (2013.01); *G02B 6/0008* (2013.01); *F21W 2131/411* (2013.01); *G01N 2201/062* (2013.01)

(56) References Cited

U.S. PATENT DOCUMENTS

| | | | | |
|---|---|---|---|---|
| 5,101,954 A * | 4/1992 | Nambu | .................. | B65B 23/06 198/370.04 |
| 6,464,195 B1 * | 10/2002 | Hildebrandt | .......... | G06F 1/1616 248/460 |
| 2003/0227613 A1 * | 12/2003 | Hebrank | .................. | C12N 7/00 356/52 |
| 2008/0252877 A1 * | 10/2008 | Kok | .................... | G01N 21/314 356/53 |

* cited by examiner

EGG CANDLING DEVICE

TECHNICAL FIELD

The present invention relates to an egg candling device in which sperm eggs and infertile eggs can be selected from eggs used in raw materials for producing vaccine for influenza, vaccine for animals and the like, and further growth excellence eggs and abnormally developed eggs can be selected from the sperm eggs, selectively automatically or manually.

BACKGROUND OF THE ART

Patent Document No. 1 (JP2008-256424 A) by the applicant constitutes basics of the present invention. For instance, as shown in FIG. 6, an egg candling device is constituted of an egg input and alignment unit 2 on which a plurality of trays 10 are installed where sperm eggs as a specimen material are arranged. A first examination part 3 is for selecting whether eggs in the trays 10 are sperm eggs or not and further whether the sperm eggs are excellence developed eggs or not. An extracting abnormally developed eggs part 4 extracts infertile eggs and abnormally developed eggs due to information from the first examination part 3, picking them from the tray 10 and disposing of them is a disposal box 5. An excellent eggs compensating part 6 automatically compensates for the removed eggs by filling in tested excellence developed sperm eggs into the trays 10 where the infertile eggs and the abnormally developed eggs were picked away. A second examination part 7 reexamines eggs including the growth excellent sperm eggs supplied from the excellent eggs compensating part 6 so as not to have any examination errors to increase accuracy of the examination, and an egg takeoff part 8 for keeping the trays 10 in which the excellent eggs are filled into parts where the abnormal eggs were removed by re-examination in the second examination part 7.

In the first examination part 3 and the second examination part 7 of the automatic sperm egg candling device 1, eggs to be tested which are moved on the tray 10 are brought up in every column of the eggs automatically or manually and the light radiates every eggs in order to judge whether the eggs are infertile eggs or sperm eggs by conditions or shadows of transmitted light through them and further to judge whether the eggs are growth excellence eggs or abnormally developed eggs, and moreover, as shown in FIG. 6, the case of visual judgment by workers for examination or the case of automatic judgment by image treatment are carried out selectively.

SUMMARY OF THE INVENTION

In the prior egg candling device as described above, though a halogen lamp is used for radiating light to the eggs, because the halogen lamp has a short life-span, there is a demand such as to want to use a LED illuminant with a long life-span, but because the light of the LED illuminant is blue, it is a problem whether a luminescent color of the LED is available to the egg candling or not.

Besides, in the prior lift-up mechanism, though a rubber cup corresponding to every egg is brought up and egg candling is performed by pressing the eggs to light fibers, because sizes of eggs are various, it was necessary that the eggs moved up and down about three times in order to bring eggs up to a suitable position.

Therefore, the present invention is to provide an egg candling device having a constitution such that an LED illuminant can be used as a light source, and to comprise a lift mechanism for bringing up the eggs to a suitable position.

Accordingly, the egg candling device according to the present invention comprises at least an egg input and alignment unit for positioning a tray on which eggs to be tested are taken out from an incubator on a moving means, an egg candling unit for identifying defective eggs by determining the quality of the eggs in the tray transported from the egg input and alignment unit, and a disposal unit for extracting and disposing eggs determined to be defective by the egg candling unit, wherein the egg candling unit comprises light sources disposed at the top, a lifting unit for lifting up eggs in the tray from below the tray so as to cause the eggs to abut the light source, a determining unit for determining the quality of eggs irradiated by the light source, and a notification means for specifying the position of eggs determined by the determined unit to be defective and notifying the disposal unit, wherein the lift unit comprises egg holding bases having diameters smaller than the diameters of the eggs, moving means for moving the eggs holding bases up and down, and egg holding parts that are disposed at prescribed intervals on the periphery of each egg holding base and that are formed from plate-like elastic members extending a prescribed length upward from the egg holding base. Especially, it is preferred that four plate-like elastic members are arranged around the egg holding base at every 90°. Furthermore, the plate-like elastic members are preferably plastic plate springs.

Thus, when bringing up the eggs to be tested, since plate-like elastic members extending upward from the periphery of the egg holding base in the lift unit bring the egg up so as to fold the egg by opening outward along a lower side surface of the egg, different sizes of the eggs are absorbed because the plate-like elastic members can be bent outward along sizes of the eggs, so that it is possible to reliably contact the eggs with the light sources.

Besides, in the present invention, it is preferred that the light sources comprise an LED source as a light source and further comprise light fibers each of which having a radiation side end that contacts with the eggs to be tested, and a receiver side end positioned to the light source side. A filter glass with orange color is interposed between the LED light source and the receiver side end.

Thus, because a condition similar to the prior halogen lump can be made, egg candling similar to the prior art can be performed without using a halogen lamp.

Moreover, in the present invention, it is preferred that the determining unit determine good and bad eggs to be tested by visual contact as the judge. Notification means notifies positions of the defective eggs to the disposal unit by pushing switches corresponding to the locations of eggs visually determined to be defective eggs as indicated by the switches located at the positions corresponding to the eggs to be tested that are lifted.

Furthermore, in the present invention, it is preferred that a switch panel on which the switches are arranged is slanted to a judge side at a specific angle and that the angle is 15°. Especially, in the case of a perched system for the judge to work at siting on, this slant switch panel is effective.

Moreover, in the present invention, it is preferred that the determining unit be an image treatment system for determining eggs to be tested by an image treatment, and for notifying positions of the defective eggs to the disposal unit.

In the present invention, it is preferred that the determining unit have both manual operation and automatic operation.

Furthermore, it is preferred that the determining unit is a first determining unit, and that a second determining unit for determining good and bad eggs to be tested is provided after the disposal unit.

In this case, it is preferred that both the first determining unit and the second determining unit can operate either in automatic system and manual mode, or, it is preferred that one of them be an automatic system and another of them be a manual system by visual contact of the judges.

According to the present invention, the eggs can be reliably contacted with the light sources since the eggs can be lifted so as to be folded by plate-like elastic members. The resulting effect is such that a resulting test period is shortened. Furthermore, because LED light is used as a light source, a lifetime of the light source can be prolonged, and the test otherwise similar to the prior test can be performed by using a filter glass with orange color.

BRIEF DESCRIPTION OF DRAWINGS

FIG. 2A shows a condition before and after lifting the eggs to be tested and FIG. 2B shows a condition of lifting the eggs to be tested;

FIG. 3A is a front view thereof and FIG. 3B is a plan view thereof;

DETAILED DESCRIPTION OF THE INVENTION

Figure 1:
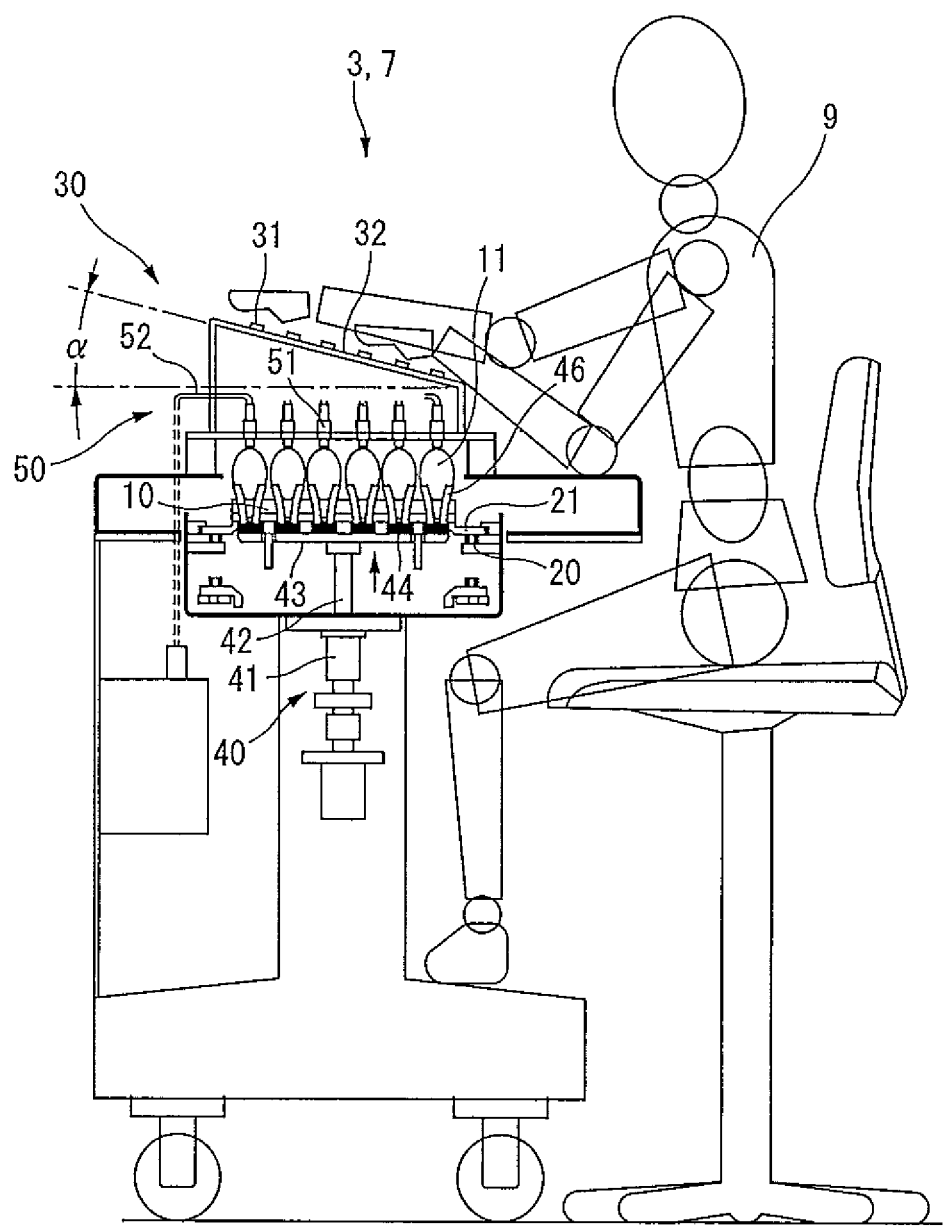
FIG. 1 is a schematic view showing the constitution of an egg candling unit according to the present invention.

Hereinafter, a working example is explained by referring to the drawings.

Figure 6:
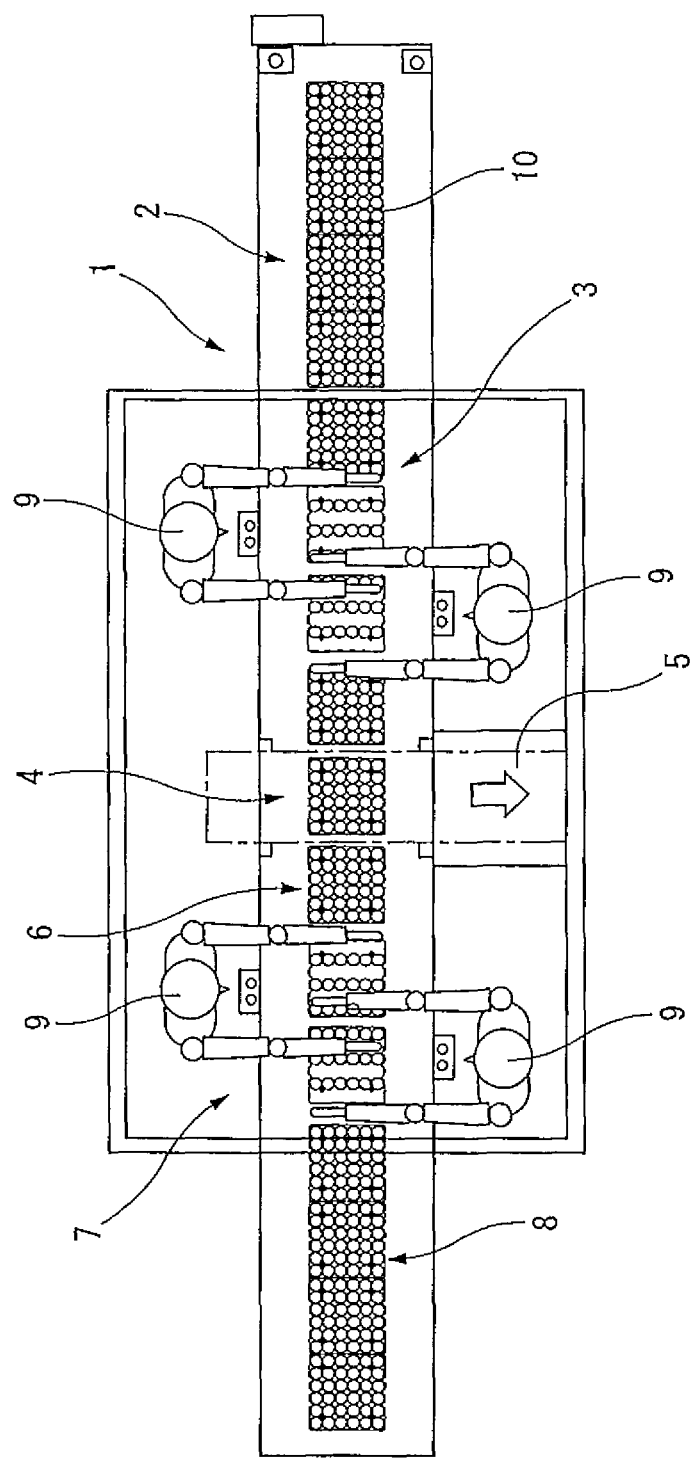
FIG. 6 is an explanatory diagram explaining the prior art system as it relates to the present invention.

A egg candling device 1 according to the present invention is constituted of, as shown in FIG. 6, an egg input and alignment unit 2 that a plurality of trays 10 on which sperm eggs are arranged as a specimen material are installed thereon, a first egg candling unit 3 for selecting sperm eggs or infertile eggs among the eggs to be tested and selecting growth excellence eggs or abnormally developed eggs among the sperm eggs, a defective egg picking-up unit 4 receiving information from the first egg candling unit 3, picking up the infertile eggs and the abnormally developed eggs and disposing them to a disposal box 5, an excellent egg loading unit 6 automatically loading growth excellence sperm eggs to have been tested to empty spaces in the tray 10 after picking up the infertile eggs and abnormally developed eggs, a second egg candling unit 7 re-testing eggs including the growth excellence sperm eggs supplied from the excellent egg loading unit 6 in order to increase precious testing of the growth excellence eggs, and an egg takeoff unit 8 holding the tray 10 in which only excellence eggs are packed after removing the defective eggs that have been retested by the second determining unit 7. Besides, in FIG. 6, the working mode in that defective eggs (infertile eggs and abnormally developed eggs) are selected visually by the workers (judges) 9 is shown, but an automatic system that an image treatment system for selecting the defective eggs by the image treatment is provided to select them automatically can be selected.

The first egg candling unit 3 and the second egg candling unit 7 according to the present invention have the same constitution, for instance, that is shown in FIG. 1. Each of the egg candling units 3 and 7 is basically constituted of a determining unit 30, a lift unit 40 and a light source 50.

Figure 2A:
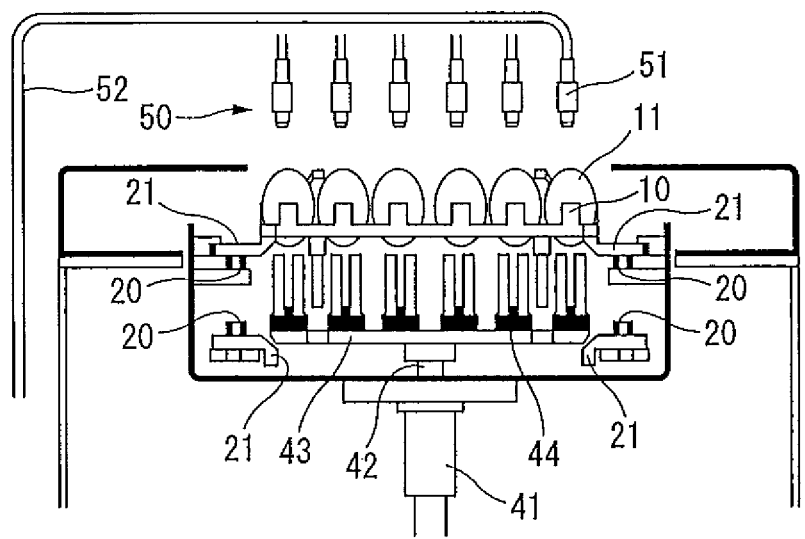
FIGS. 2A and 2B are explanatory diagrams showing the constitution of a lift unit according to the present invention, especially
Figure 2B:
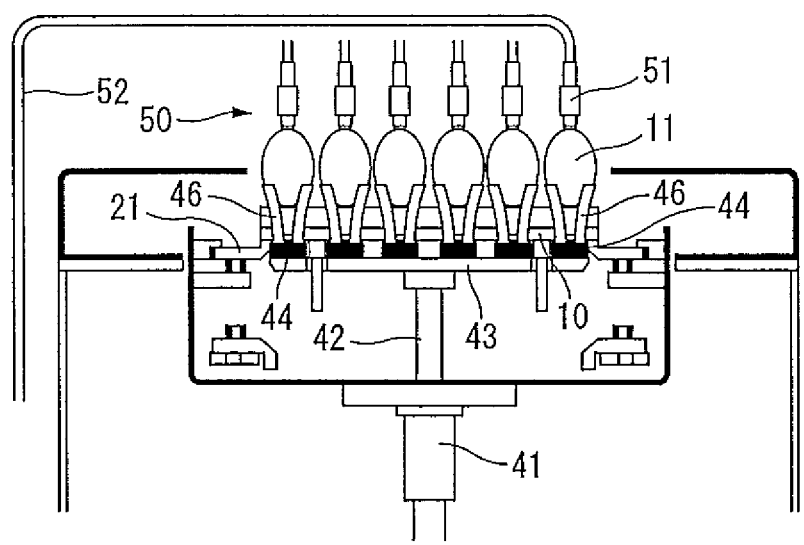

The lift unit 40 comprises, as shown in FIG. 1, FIG. 2A and FIG. 2B, an air cylinder 41 driven with fluid, especially by gas (air), a connection part 43 located at a top of a moving rod 42 of the air cylinder 41 and tested egg holding units 44 located at positions corresponding to a plurality of tested eggs 11 installed on the tray 10 on the connection part 43.

Figure 3A:
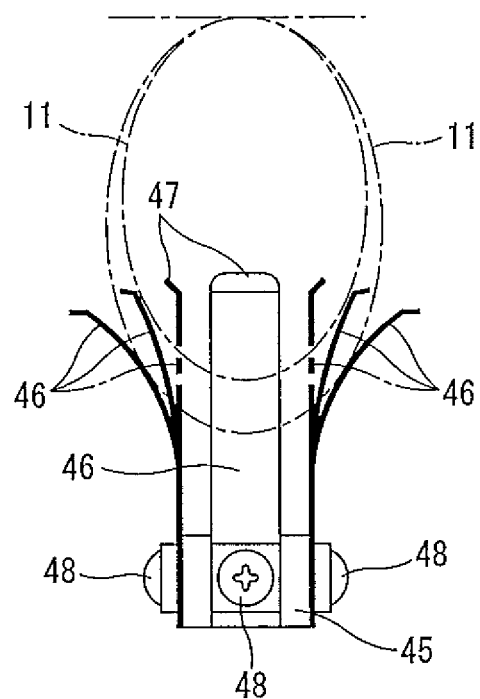
FIGS. 3A and 3B are explanatory diagrams showing the constitution of an egg holding base of a lift unit, especially
Figure 3B:
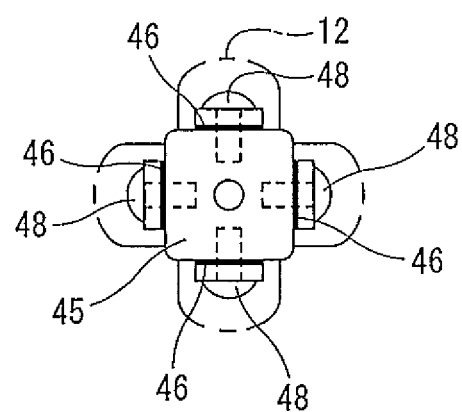

The tested egg holding unit 44 comprises, as shown in FIGS. 3A and 3B, a base 45 whose plane surface united with or connected to the connection part 43 is approximately square and having smaller size than shorter diameters of the tested eggs, and plate-like elastic members 46 fixed on four side surfaces of the base 45 (side surfaces positioned around the base at every 90°) and extending upward, respectively. The plate-like elastic members 46 rise up corresponding to rise of the moving rod 42, after their top ends are contact with a lower part of the tested egg 11, they are spread outward along a lower side surface of the tested egg 11, so that the tested egg 11 is brought up so as to fold below by the four plate-like elastic members 46. Besides, it is preferred that a tapered part 47 slant outward is formed at a top of every plate-like elastic member 46. Furthermore, since opening angles of the plate-like elastic members 46 can vary corresponding to sizes of eggs 11, contact positions to the radiation side end 51 of the eggs 11 can become constant. Moreover, the plate-like elastic members are preferably formed with plastics.

Figure 4:
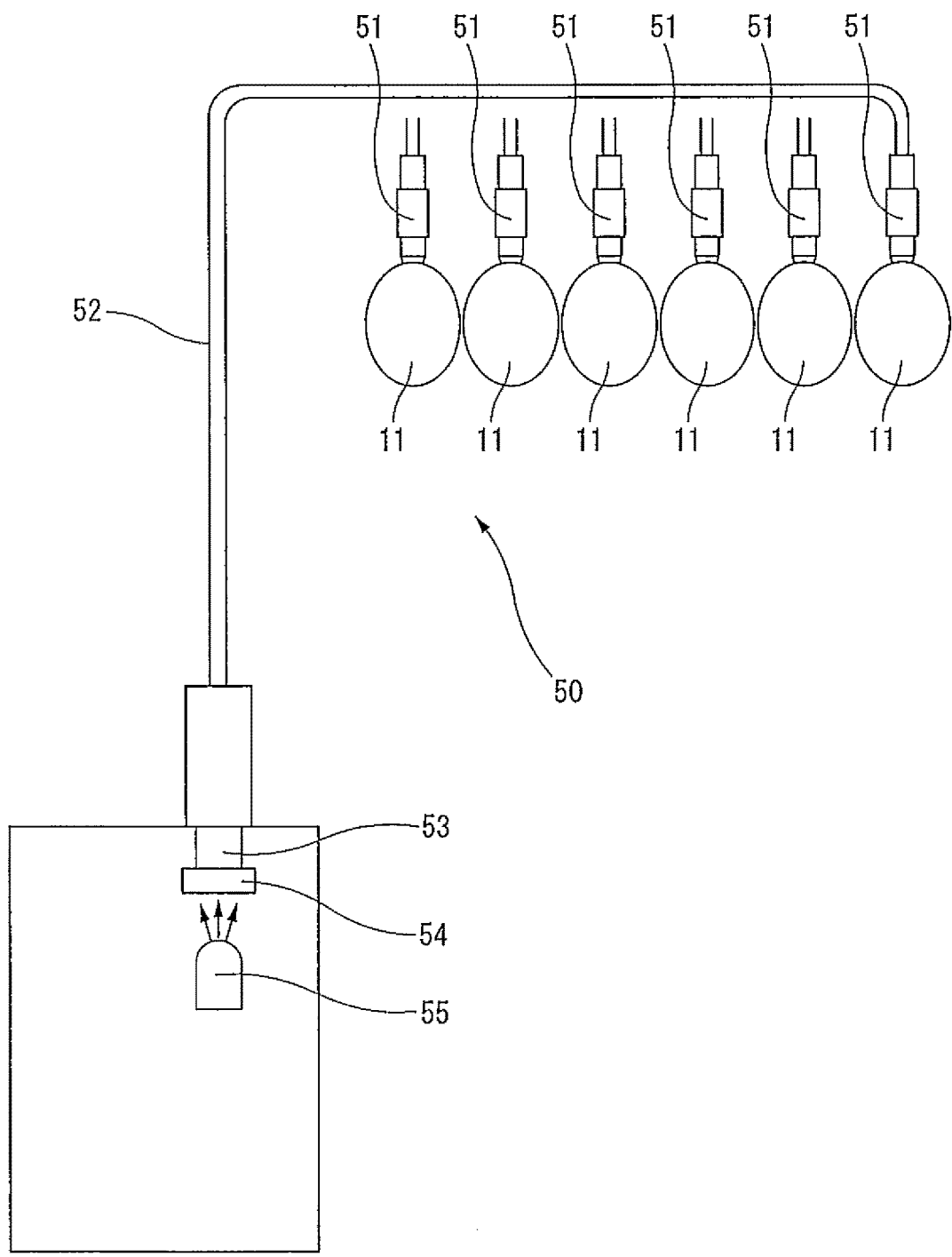
FIG. 4 is an explanatory diagram showing the constitution of light sources according to the present invention.

The light source 50 comprises, for instance, as shown in FIG. 1, FIG. 2 and FIG. 4, light fibers 52 having radiation side ends 51 on which the top ends of the tested eggs lifted up by the tested egg holding units 44 and receiver side end 53 positioning to a light source side and receiving light from an LED light source 55, and further comprises a filter glass 54 with orange color intervening between the LED light source 55 and the receiver side end 53 of the light fibers 52. Besides, it is preferred that the radiation side end 51 has an optical control means such as a field lens, a diaphragm or the like, and thus, it is preferred that intensity and diffuseness of light radiated to the tested eggs 11 can be fine-tuned.

The determining unit 30 is to select detective eggs (infertile eggs and abnormally developed eggs) by visual contact of a judge 9 from image or shadow condition projected by light radiating from the light source 50 or image judgment by the image treatment system, and, in the case of visual contact of the judge 9, comprising a plurality of switches 31 used by the visual contact and a switch panel 32 on which the switches 31 are arranged corresponding to positions of the tested eggs 11. Besides, in the automatic egg candling, a camera or cameras for taking images of the tested eggs by radiated light is/are provided beside positions where the tested eggs are contact with radiation side end 51 when the tested eggs 11 go up, and thus, images taken by the camera(s) are treated in order to specify the defective eggs and transmitting the position information to the next defective egg picking-up unit 4. Besides, in the case of visual judgment of the judge 9, when the defective eggs are determined, the judge 9 pushes the switch 31 at position corresponding to the determined defective egg and transmits the position information to the next defective egg picking-up unit 4.

Furthermore, as shown in FIG. 1, it is preferred that the switch panel 32 is slant at a specific angle α toward to the judge side in order to increase workability. The angle α is, for instance, 15°.

Figure 5:
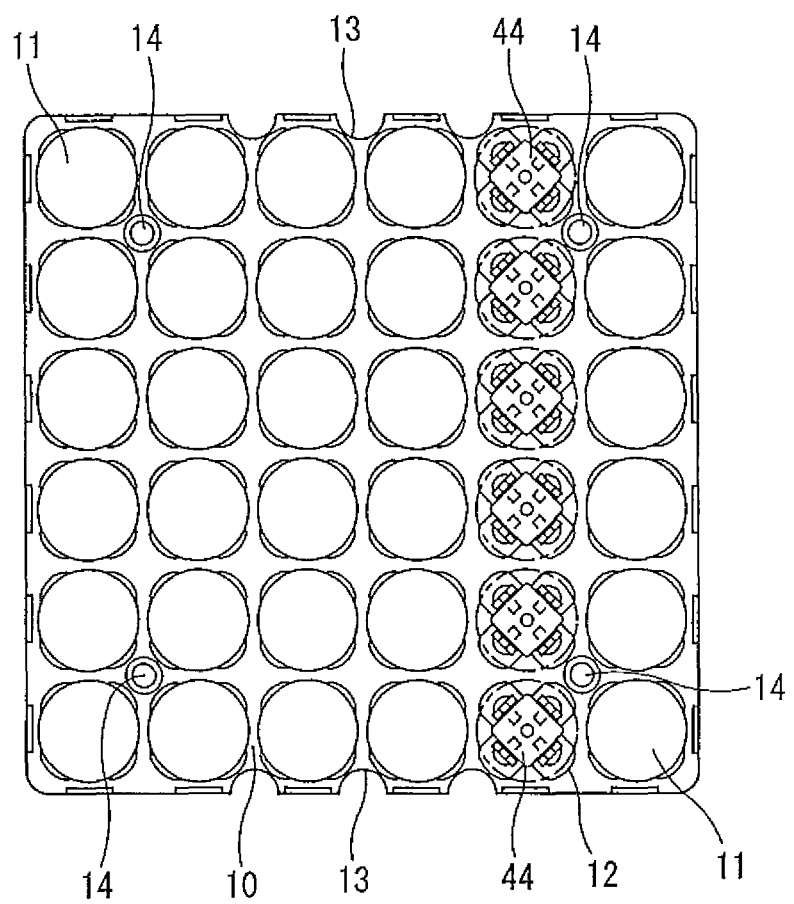
FIG. 5 is an explanatory diagram showing the constitution of a tray used in the present invention.

As the above mentioned constitution, plural eggs to be tested are installed on the tray 10 shown in FIG. 5. This tray 10 has openings 12 formed below parts on which the eggs 11 are installed. Furthermore, cutouts 13 on which levers 21 of moving chains 20 are hung up are formed in the tray 10 and supporting rods 14 is provided so as not to crash eggs 11 when the trays 10 are stuck up.

The trays 20 on which the eggs to be tested are installed move to the first egg candling unit 3 and stop there. When the judge 9 pushes the examination switch, the cylinder 41 is driven and the tested egg holding unit 44 brings up the eggs to be tested to be contact with the radiation side ends 51, and light radiates to the tested eggs 11 from the light source. The judge 9 determines whether the eggs to be tested are growth excellence eggs or defective eggs (infertile eggs and abnormally developed eggs) from images or shadows gained by the radiated light. In the case that the egg is an defective egg, the judge 9 pushes the switch on the switch panel 32 corresponding to the defective egg and the signal by the switch are transmitted to the next defective egg picking-up unit 4. The eggs 11 to have been tested are brought back to the tray 10 and the tray 10 moves from the first egg candling unit 3 to the defective egg picking-up unit 4.

In the defective egg picking-up unit 4, a rubber absorption pad corresponding to the defective egg based on the signal from the first egg candling unit 3 among the rubber absorption pads located corresponding to the tested eggs 11 above the tested eggs on the tray 10 goes down and absorbing the defective egg to bring up and move, and further dispose it to the disposal box 5. Besides, in the excellent egg loading unit 6 next to the defective eggs picking-up unit 4, the excellent eggs are loaded into empty spaces where the defective eggs are removed to fill the tray 10.

This tray 10 is transported to the second egg candling unit 7, and the operation similar to the operation in the first egg candling unit 3 is performed so that no defective egg is present in the tray 10. Thus, the tray 10 without defective eggs moves to the egg takeoff unit 8 and waits.

Due to the above, according to the egg candling unit of the present invention, accuracy of the egg candling and workability can be increased surely.

EXPLANATION OF LETTERS OR NUMERALS

1 Egg Candling Device
2 Egg Input and Alignment Unit
3 First Egg Candling Unit
4 Defective Egg Picking-up Unit
5 Disposal Box
6 Excellent Egg Loading Unit
7 Second Egg Candling Unit
8 Egg Takeoff Unit
9 Judge
10 Tray
11 Tested Egg
12 Opening
13 Cutout
14 Supporting Rod
30 Determining Unit
31 Switch
32 Switch Panel
40 Lift Unit
41 Air Cylinder
42 Moving Rod
43 Connection Part
44 Tested Egg Holding Unit
45 Base
46 Plate-like Elastic Member
47 Taper
48 Screw
50 Light Source
51 Radiation Side End
52 Light Fiber
53 Receiver Side End
54 Filter Glass

The invention claimed is:

1. An egg candling device for determining goodness or badness of eggs to be tested in a transported tray of eggs and for specifying defective eggs, the egg candling device comprising:
   a disposal unit to pick up and dispose of eggs determined as defective eggs in an egg candling unit, wherein said egg candling unit comprises:
      plurality of light sources arranged above the transported tray of eggs,
      a lift unit, installed below the transported tray of eggs, to lift up the eggs to be tested from the transported tray of eggs to place the eggs to be tested in contact with respective ones of the plurality of light sources,
      a determining unit for determining the goodness or badness of the eggs to be tested using illumination by the plurality of light sources, and
      notification means for specifying a position of each egg determined as a defective egg by the determining unit and notifying the position of each defective egg to the disposal unit,
   wherein the lift unit comprises:
      a plurality of egg holding bases each having a smaller diameter than diameters of the eggs to be tested,
      moving means for moving the plurality of egg holding bases up and down, and
      a tested egg holding unit comprising a plurality of planar members of elastic material provided around each respective one of the plurality of egg holding bases at specific intervals and extending to a specific length above said egg holding bases.

2. An egg candling device according to claim 1, wherein the plurality of light sources comprise:
   an LED light source, and
   a plurality of light fibers each of which has a radiation side end contacting with the egg to be tested and a receiver side end collecting light from the LED light source, and
   a filter glass with orange color interposed between the LED light source and the receiver side ends of said plurality of light fibers.

3. An egg candling device according to claim 1, wherein:
   the determining unit has a mode to enable detection of the goodness or badness of the eggs to be tested by visual inspection, and
   the notification means notifies the position of the defective egg to the disposal unit by a pushed switches positioned corresponding to the egg determined as defective by visual contact, the pushed switch being among a plurality of switches positioned corresponding to the plurality of eggs to be tested.

4. An egg candling device according to claim 2, wherein:
   the determining unit has a mode to enable detection of the goodness or badness of the eggs to be tested by visual inspection, and
   the notification means notifies the position of the defective egg to the disposal unit by a pushed switch positioned corresponding to the egg determined as defective by visual contact, the pushed switch being among a plurality of switches positioned corresponding to the plurality of eggs to be tested.

5. An egg candling device according to claim 3, further comprising:
   a switch plate on which the plurality of switches are arranged, the switch plate being slanted toward an inspector.

6. An egg candling device according to claim 4, further comprising:
   a switch plate on which the plurality of switches are arranged, the switch plate being slanted toward an inspector.

* * * * *